United States Patent [19]

Jouffret

[11] 4,223,165
[45] Sep. 16, 1980

[54] PROCESS FOR THE HYDROXYLATION OF AROMATIC COMPOUNDS

[75] Inventor: Michel Jouffret, Francheville le Bas, France

[73] Assignee: Rhone-Poulenc Industries, Paris, France

[21] Appl. No.: 889,352

[22] Filed: Mar. 23, 1978

Related U.S. Application Data

[63] Continuation of Ser. No. 707,025, Jul. 20, 1976, abandoned.

[30] Foreign Application Priority Data

Jul. 25, 1975 [FR] France .................................. 75 23313

[51] Int. Cl.$^2$ ....................... C07C 37/00; C07C 39/10
[52] U.S. Cl. .................................................... 568/771
[58] Field of Search .................... 260/613 D; 568/771

[56] References Cited

U.S. PATENT DOCUMENTS

| 3,816,545 | 6/1974 | Block | 260/621 G |
| 3,849,502 | 11/1974 | Bourdin et al. | 260/613 D |

Primary Examiner—Werren B. Lone
Attorney, Agent, or Firm—Burns, Doane, Swecker & Mathis

[57] ABSTRACT

Aromatic hydrocarbons and particularly phenols and phenol ethers can be hydroxylated by reacting the aromatic compound with hydrogen peroxide in a reaction medium comprising trifluoromethanesulfonic acid. High yields of hydroxylated aromatic compounds are obtained by this process which avoids the use of extremely corrosive and difficult to handle agents. Phenol is hydroxylated predominantly to hydroquinone by this process.

15 Claims, No Drawings

PROCESS FOR THE HYDROXYLATION OF AROMATIC COMPOUNDS

This is a continuation of application Ser. No. 707,025, filed July 20, 1976 now abandoned.

BACKGROUND OF THE INVENTION

(1) Field of the Invention

This invention relates to a process for the hydroxylation of aromatic compounds and more particularly to a process for hydroxylating phenols and phenol ethers using hydrogen peroxide.

(2) Description of the Prior Art

Numerous process have been described for oxidizing phenols and phenol ethers with hydrogen peroxide in combination with metal salts, or with organic peracids (formed from hydrogen peroxide and a carboxylic acid). According to the circumstances, these process have allowed a hydroxyl radical to be introduced into the nucleus of the aromatic compound, or have brought about a more or less extensive oxidation of this nucleus, ranging from the production of quinones to the opening of the benzene ring with the formation of degradation products.

Thus, A. Chwala et al., J. Prakt. Chem. 152, 46 (1939) oxidized phenol with hydrogen peroxide in the presence of ferrous sulphate, in water acidified with sulphuric acid, to give a mixture of hydroquinone and pyrocatechol with a yield of 72% relative to the hydrogen peroxide used in the reaction. In spite of the good yields which it produces, this process has no industrial value on account of, firstly, the particularly prolonged contact times which it requires, which are the result of having to operate at the temperature of ice-cold water, and, secondly, the very great dilution of the reaction medium necessitated by this type of reaction. Moreover, it has been pointed out by Stein, J. Chem. Soc. 1951 3266 that reaction must be conducted under relatively mild conditions to avoid a violent reaction leading to benzoquinone.

G. G. Henderson et al., J. Chem. Soc. 91 1659.69 (1910), proposed oxidizing phenols with hydrogen peroxide in acetic acid which acted as solvent and provided peracetic acid. In the case of phenol, a reaction of several days at ambient temperature was necessary to obtain a mixture of hydroquinone, pyrocatechol and p-benzoquinone. Under analogous conditions, cresols lead to tarry products containing dihydroxymethylbenzenes.

The oxidation of various phenol ethers with organic peracids has also been carried out. Depending on the circumstances, these ethers were converted into quinones or even further oxidized with the opening of the aromatic ring, or, in some cases, were not even sensitive to the oxidizing agent, see S. L. Friess et al. J. Am. Chem. Soc. 74 1305 (1952); H. Fernholz, Chem. Ber. 87 578 (1954); H. Davidge et al., J. Chem. Soc. 1958 4569. Anisole and its homologues were not converted, or led to unidentified water-soluble products.

J. D. McClure et al. (J. Org. Chem. 27 627–8 (1962)) oxidized anisole and diphenyl ether in methylene chloride with trifluoroperacetic acid. The reaction did in fact allow phenolic hydroxy groups to be introduced into the aromatic nucleus, but the yields obtained were moderate; in the case of anisole, a mixture of isomeric methoxyphenols was obtained, with a yield of 34% relative to the phenol ether. However, the preparation of trifluoroperacetic acid is dangerous and can give rise to explosions.

U.S. Pat. No. 3,849,502 has proposed a process for the hydroxylation of phenols and their ethers by means of hydrogen peroxide, in the presence of traces of a strong acid and preferably with an agent which complexes the metal ions, such as orthophosphoric acid and polyphosphoric acid. Treatment of the phenol in accordance with this patented process gives a mixture of hydroquinone and predominantly of pyrocatechol.

Processes employing hydrogen peroxide associated with hydrofluoric acid have also been proposed for introducing a hydroxyl radical on an aromatic nucleus. U.S. Pat. No. 3,461,170 discloses the hydroxylation reaction carried out in the presence of substantially anhydrous hydrofluoric acid. The hydrofluoric acid process was then improved by adding a catalyst modifier such as alkanesulfonic acids or arylsulfonic acids as disclosed in U.S. Pat. No. 3,816,545 or trifluoroacetic acid as taught in published French Application No. 2,216,254 or by addition of a solvent chosen from the group consisting of the nitroalkanes, the aromatic nitro compounds, aniline and sulfolane as disclosed in U.S. Pat. No. 3,839,467. These processes make it possible to obtain better selectivity of the reaction, with respect to hydroquinone, when phenol is the aromatic compound hydroxylated. However, such processes require substantial amounts of hydrofluoric acid, which then becomes the reaction medium. In these large amounts the processes employing hydrofluoric acid are difficult to carry out since extreme care is required in handling this reactant. Furthermore, industrial development of such processes is hampered since hydrofluoric acid presents severe corrosion problems to equipment.

Thus, industry has no simple method available for introducing hydroxyl radicals into an aromatic nucleus with hydrogen peroxide. In particular, existing processes for hydroxylating phenols, particularly phenol itself, in aqueous media, require dilution conditions which remove all industrial character from these processes, and, when these conditions are not adhered to, do not allow the desired products to be obtained. Furthermore, the use of an excess acid, when hydroxylation is achieved with a peracid, complicates the recovery of the products formed.

SUMMARY OF THE INVENTION

The present invention provides a process for the hydroxylation of aromatic compounds of the formula:

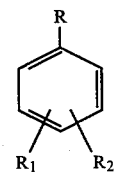

in which R, $R_1$ and $R_2$, are independently selected from the group consisting of hydrogen and alkyl containing from 1 to 3 carbon atoms, and R also represents a hydroxyl or an alkoxy containing from 1 to 3 carbon atoms, which comprises reacting said aromatic compound with hydrogen peroxide, at hydroxylating conditions in a reaction medium comprising trifluoromethanesulfonic acid.

It is therefore an object of this invention to provide an improved process for obtaining hydroxylated aromatic compounds.

Another object of this invention is to provide a process for preparing hydroxylated aromatic compounds by effecting the hydroxylation in a medium comprising trifluoromethanesulfonic acid.

Another object of this invention is to provide an improved process for the hydroxylation of phenol and phenol ethers.

A further object of this invention is to provide a process for preparing hydroxylated aromatic compounds which does not promote severe corrosion problems.

A still further object of this invention is to provide a hydroxylation process of phenol which results predominantly in hydroquinone.

Other objects and embodiments of this invention will be found in the following further detailed description thereof.

DESCRIPTION OF THE PREFERRED EMBODIMENTS

It is hereinbefore set forth that the present invention is concerned with a process for introducing hydroxyl substituents on the ring of an aromatic compound, said hydroxylation being effected by treating an aromatic compound with hydrogen peroxide in a reaction medium comprising trifluoromethanesulfonic acid. More particularly, this invention provides a process for hydroxylating an aromatic compound of the formula:

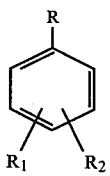

in which R, $R_1$ and $R_2$ are independently selected from the group consisting of hydrogen and alkyl containing from 1 to 3 carbon atoms, and R also represents a hydroxyl or alkoxy containing from 1 to 3 carbon atoms which comprises reacting said aromatic compound with hydrogen peroxide at hydroxylating conditions in a reaction medium comprising trifluoromethanesulfonic acid.

In the formula of the aromatic compounds defined above, R, $R_1$ and $R_2$ may represent a methyl, ethyl or any of the isomeric propyl radicals. Benzene, toluene, ethylbenzene, cumene, the xylenes, mesitylene, pseudocumene, phenol, the cresols, and alkoxyphenols such as, anisole, phenetole, guaiacol and p-methoxyphenol are suitable starting materials.

The molar ratio of hydrogen peroxide to the aromatic compound used can vary from 0.025 to 0.3 and preferably between 0.05 and 0.2. The degree of conversion of the aromatic compound depends on this ratio. It has been found that the degree of conversion varies directly proportional to the amount of hydrogen peroxide used. However, it is preferable to limit the degree of conversion to 30% and preferably to 15% not to affect the yield of hydroxylic products.

The initial water content of the reaction mixture must be less than 5%. This water can be introduced into the reaction medium by the reactants used. It is advantageous to operate with an aqueous solution which contains at least 50% by weight of hydrogen peroxide in order to introduce less than 5% by weight of water into the reaction medium. It is preferable to introduce the hydrogen peroxide as a solution in trifluoromethanesulfonic acid in order to achieve better control of the reaction and to obtain high reaction outputs. The concentration of hydrogen peroxide in solution in the trifluoromethanesulfonic acid, expressed as weight of pure hydrogen peroxide relative to the weight of the trifluoromethanesulfonic acid, is generally between 1 and 30% and preferably between 2.5 to 25% of hydrogen peroxide.

The concentration of the trifluoromethanesulfonic acid used in general is not critical since the trifluoromethane serves as the reaction medium. It has been found that a volume ratio of trifluoromethanesulfonic acid to aromatic compound of at least 0.25 is very suitable. It is appropriate for economic reasons to select volume ratios of trifluoromethanesulfonic acid to aromatic compound not to exceed 20.

The reaction can be carried out in the presence of another organic solvent such as, chloroform, nitrobenzene or dichloroethane, especially when the temperature chosen is below the melting point of the aromatic compound in order to obtain a more fluid reaction mixture.

According to a preferred practical embodiment of the invention, the solution of hydrogen peroxide in trifluoromethanesulfonic acid is added gradually to the reaction mixture consisting of the aromatic compound and the trifluoromethanesulfonic acid which may contain a complexing agent, the mixture being heated beforehand to the reaction temperature.

The process according to the invention can be carried out at temperatures of between $-40°$ and $10°$ C. and preferably between $-20°$ and $0°$ C.

It has been found that the presence of metal ions is prejudicial to the process of the invention taking place satisfactorily, particularly in the case of phenols, where the yields of hydroxylation products are low. Consequently, it is preferable to inhibit the action of metal ions.

The chemically active metal ions which are detrimental to the hydroxylation taking place satisfactorily, are the ions of transition metals, particularly iron, copper, chromium, cobalt, manganese and vanadium ions. The metal ions are derived from the reactants, especially the aromatic compounds, and by the apparatus used. In order to inhibit the action of these metal ions, the reaction may be carried out in the presence of one or more complexing agents which are stable to hydrogen peroxide, which give complexes which cannot be decomposed by the strong acids present, and in which the metal can no longer exert any chemical activity. Moreover, it is immaterial whether the complexing agents (or ligands) lead to complexes which are soluble or which are insoluble in the reaction medium. The complexing agent or agents introduced into the reaction medium are selected as a function of the metals present and of their ability to form stable complexes under the reaction conditions. The complexing agents which are suitable for a particular case can be determined by means of simple tests. Complexing agents such as phoshoric acids (ortho, meta or pyrophosphoric acids or their mixtures) and their alkyl, cycloalkyl or alkaryl acid esters containing up to about 10 carbon atoms in the alkyl portion e.g. ethyl, diethyl, methyl, hexyl, cyclohexyl, benzyl, octyl or ethylhexyl phosphates, and polyphosphoric acids, may be used.

The amount of complexing agent present in the reaction medium depends on the content of metal ion in this medium. There is no upper limit to the amount of complexing agent that can be used and the amount can be greatly in excess over the amount necessary to complex the metal ions present. In practice, an amount which is from 0.00001 to 5% by weight of the reaction medium is very suitable.

The following examples are given to illustrate the invention:

EXAMPLE 1

In this example 0.0425 g of orthophosphoric acid containing 85% by weight of pure acid is charged into a 50 cm$^3$ beaker equipped with a 3 cm$^3$ microburette and a thermometer, the contents are mixed with a magnetic stirrer, 2.2 cm$^3$ (2.35 g) of molten phenol are introduced by pipette and 19.8 cm$^3$ (33.58 g) of trifluoromethanesulfonic acid are charged under a nitrogen atmosphere.

The reaction mixture is cooled to $-21°$ C. by immersing the beaker into a mixture of acetone and solid carbon dioxide. After cooling, 1.2 cm$^3$ (2.0347 g) of a solution of hydrogen peroxide in trifluoromethanesulfonic acid, prepared by diluting 0.2527 g of 84.7% strength by weight hydrogen peroxide with 9.9282 g of trifluoromethanesulfonic acid cooled to $-20°$ C., is then gradually charged to the reaction mixture over a two minute period.

After stirring for 10 minutes at $-10°$ C., the reaction mixture is poured slowly into a 100 cm$^3$ beaker containing 32 cm$^3$ of an aqueous solution of potassium acetate (980 g/l). The reaction is exothermic and the reaction mixture is cooled so as to maintain a temperature below 30° C. The neutralized solution is then charged into a liquid-liquid extractor and is extracted with ether under a nitrogen atmosphere continuously for a period of 4 hours.

The ether solution is distilled to about 50 cm$^3$ and is then adjusted to 100 cm$^3$ with ethyl acetate. This solution is analyzed by chromatography on an alumina column.

The overall yield of diphenols amounts to 74.7% relative to hydrogen peroxide. The yield of hydroquinone (HQ) and pyrocatechol (PC) amounts to 51% and 23.7%, respectively, which represents an HQ/PC selectivity of 2.15.

EXAMPLES 2 TO 8

The process of Example 1 is repeated under the conditions and with the results, recorded in TABLE I below:

TABLE I

| Example | Reactants | $H_2O_2$ in $CF_3SO_3H$ (wt %) | Degree of conversion | Rate of $H_2O_2$ Addition (seconds) | Temp. °C. | Yields HQ % | PC % | HQ + PC % | Selectivity Ratio HQ/PC |
|---|---|---|---|---|---|---|---|---|---|
| 2 | Phenol : 2.2 cm$^3$<br>$CF_3SO_3H$:19.8 cm$^3$<br>$H_2O_2$ : 0.175 cm$^3$ | 22 | 7.1% | 180 | $-10$ | 43.7 | 21.8 | 65.5 | 2 |
| 3 | Phenol : 2.2 cm$^3$<br>$CF_3SO_3H$:19.8 cm$^3$<br>$H_2O_2$ : 0.6 cm$^3$ | 4.8 | 5.4% | 60 | $-12/-15$ | 48 | 28 | 76 | 1.71 |
| 4 | Phenol : 4.4 cm$^3$<br>$CF_3SO_3H$:13.2 cm$^3$<br>$H_2O_2$ : 1.2 cm$^3$ | 4.8 | 5.5 | 150 | $-10/-14$ | 32.8 | 18 | 50.8 | 1.82 |
| 5 | Phenol : 4.4 cm$^3$<br>$CF_3SO_3H$:13.2 cm$^3$<br>$H_2O_2$ : 2.4 cm$^3$ | 2.5 | 6.2% | 330 | $-25/-14$ | 50.7 | 28.7 | 79.4 | 1.76 |
| 6 | Phenol : 4.4 cm$^3$<br>$CF_3SO_3H$:13.2 cm$^3$<br>$H_3PO_4$ : 0.465 g<br>$H_2O_2$ : 1.2 cm$^3$ | 4.5 | 5.4% | 265 | $-23/-10$ | 47.6 | 28.3 | 75.9 | 1.68 |
| 7 | Phenol : 2.2 cm$^3$<br>$CF_3SO_3H$:19.8 cm$^3$<br>$H_3PO_4$ : 0.024 g<br>$H_2O_2$ : 0.6 cm$^3$ | 4.4 | 5.1% | 60 | $-27/-20$ | 45.8 | 23.2 | 69 | 1.96 |
| 8 | Phenol : 2.2 cm$^3$<br>$CF_3SO_3H$:19.8 cm$^3$<br>$H_3PO_4$ : 0.0435 g<br>$H_2O_2$ : 2.4 cm$^3$ | 4.4 | 20.5% | 180 | $-15/-12$ | 44.6 | 14.6 | 59.2 | 3.06 |

EXAMPLES 9 AND 10

The process in Example 1 is repeated under the conditions and with the results recorded in TABLE II below. The reaction products are analyzed by gas phase chromatography after ether extraction from the reaction mixture.

TABLE II

| Example | Reactants | $H_2O_2$ in $CF_3SO_3H$ (wt %) | Degree of conversion | Rate of $H_2O$ Addition (seconds) | Temp. °C. | Yields para % | ortho % | o + p % | Selectivity Ratio p/o |
|---|---|---|---|---|---|---|---|---|---|
| 9 | Anisol : 5.5 cm$^3$<br>$CF_3SO_3H$ : 5.5 cm$^3$<br>$H_3PO_4$ : 0.0210 g<br>$H_2O_2$ : 2.4 cm$^3$ | 4.6 | 10.7% | 300 | $-20/-12$ | 37.7 | 35.4 | 73.1 | 1.06 |
| 10 | Toluene : 5.3 cm$^3$<br>$CF_3SO_3H$ : 5.3 cm$^3$<br>$H_3PO_4$ : 0.025 g<br>$H_2O_2$ : 2.4 cm$^3$ | 4.6 | 10.6 | 240 | $-17/-16$ | 26.6 | 53.7 | 80.3 | 0.5 |

I claim:

1. A process for the hydroxylation of aromatic compounds of the formula

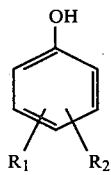

in which $R_1$ and $R_2$ are independently selected from the group consisting of hydrogen and an alkyl containing from 1 to 3 carbon atoms which comprises reacting said compound with hydrogen peroxide at a reaction temperature between about −40° and 10° C., in a reaction medium comprising trifluoromethanesulfonic acid, wherein the volume ratio between the trifluoromethanesulfonic acid and the aromatic compounds is at least about 0.25, the molar ratio of hydrogen peroxide/aromatic compound is between about 0.025 and 0.3, and the weight of pure hydrogen peroxide relative to the weight of the trifluoromethanesulfonic acid is between about 1 and 30% whereby the para-hydroxylated isomer of said compound is formed as the predominant reaction product relative to all other hydroxylated isomers of said compound.

2. The process as defined by claim 1, wherein the volume ratio of trifluoromethanesulfonic acid/aromatic compound is between 0.25 and 20.

3. The process as defined by claim 1, wherein the degree of conversion of the aromatic compound is 30% or less so as not to affect the yield of the hydroxylated products.

4. The process as defined by claim 3, wherein said degree of conversion is 15% or less.

5. The process as defined by claim 1, wherein said molar ratio of hydrogen peroxide/aromatic compound is between about 0.05 and 0.2.

6. The process as defined by claim 1, wherein the initial water content of the reaction mixture is less than 5%.

7. The process as defined by claim 6, wherein the reaction medium comprises an aqueous solution which contains at least 50% by weight of hydrogen peroxide.

8. The process as defined by claim 7, wherein said hydrogen peroxide is introduced into said reaction mixture as a solution in trifluoromethanesulfonic acid in which the concentration of hydrogen peroxide in the solution expressed as weight of pure hydrogen peroxide relative to the weight of trifluoromethanesulfonic acid is between 1 and 30%.

9. The process as defined by claim 8, wherein said concentration of hydrogen peroxide is between 2.5 and 25%.

10. The process as defined by claim 1, wherein the reaction is carried out in the presence of a complexing agent selected from the group consisting of phosphoric acids and alkyl or benzyl esters thereof, wherein the alkyl group contains 1 to 10 carbon atoms.

11. The process as defined by claim 10, wherein said complexing agent is used in an amount of 0.00001 to 5 weight percent of the reaction mixture.

12. The process as defined by claim 8, wherein said solution of hydrogen peroxide is gradually added to the reaction mixture containing a phosphoric acid.

13. The process as defined by claim 1, wherein the reaction temperature is between −20° and 0° C.

14. The process as defined by claim 1, wherein said aromatic compound is phenol.

15. The process as defined by claim 14, wherein the predominant hydroxylation product is hydroquinone.

* * * * *